US008329611B2

(12) United States Patent
Shay

(10) Patent No.: US 8,329,611 B2
(45) Date of Patent: Dec. 11, 2012

(54) TITANIA-CONTAINING EXTRUDATE

(75) Inventor: Daniel Travis Shay, Glen Mills, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 161 days.

(21) Appl. No.: 12/653,563

(22) Filed: Dec. 16, 2009

(65) Prior Publication Data

US 2011/0143927 A1 Jun. 16, 2011

(51) Int. Cl.
*B01J 31/00* (2006.01)
*B01J 21/00* (2006.01)
(52) U.S. Cl. ............... 502/172; 502/350; 502/351
(58) Field of Classification Search ............ 502/172, 502/350, 351
See application file for complete search history.

(56) References Cited

U.S. PATENT DOCUMENTS

| | | | |
|---|---|---|---|
| 3,743,607 A | 7/1973 | Sennewald | |
| 3,775,342 A | 11/1973 | Kronig et al. | |
| 4,046,832 A | 9/1977 | Nowak et al. | |
| 4,552,860 A | 11/1985 | Murib | |
| 5,194,417 A | 3/1993 | Smith et al. | |
| 5,336,802 A | 8/1994 | Smith et al. | |
| 5,804,296 A * | 9/1998 | Itoh et al. | 428/326 |
| 5,884,138 A | 3/1999 | Chalasani et al. | |
| 6,022,823 A | 2/2000 | Augustine et al. | |
| 6,316,383 B1 | 11/2001 | Tacke et al. | |
| 6,376,706 B2 | 4/2002 | Kitchen et al. | |
| 6,420,595 B1 | 7/2002 | Hallinan et al. | |
| 6,632,973 B1 | 10/2003 | Miyake et al. | |
| 6,709,570 B1 | 3/2004 | Van Crijnen-Beers et al. | |
| 6,797,669 B2 | 9/2004 | Zhang | |
| 6,803,340 B2 | 10/2004 | Lee et al. | |
| 6,992,040 B2 | 1/2006 | Muller et al. | |
| 7,387,981 B1 | 6/2008 | Kaminsky et al. | |
| 7,514,476 B2 | 4/2009 | Parasher et al. | |
| 7,521,393 B2 | 4/2009 | Blankenship et al. | |
| 7,556,793 B2 * | 7/2009 | Dahar | 423/610 |
| 7,612,244 B2 | 11/2009 | Strebelle et al. | |
| 7,638,459 B2 | 12/2009 | Rende et al. | |
| 7,648,936 B2 | 1/2010 | Morales et al. | |
| 7,674,744 B2 | 3/2010 | Shiratori et al. | |
| 7,745,370 B2 | 6/2010 | Blankenship et al. | |
| 7,811,968 B2 | 10/2010 | Augustine | |
| 7,820,583 B2 | 10/2010 | Fu et al. | |
| 7,842,641 B2 | 11/2010 | Fu et al. | |
| 7,910,517 B2 | 3/2011 | Schubert et al. | |
| 2001/0025009 A1 | 9/2001 | Fischer et al. | |
| 2002/0165092 A1 | 11/2002 | Zhang | |
| 2005/0150845 A1 | 7/2005 | Hashimoto et al. | |
| 2005/0255021 A1 | 11/2005 | Di Francesco | |
| 2007/0179310 A1 | 8/2007 | Augustine | |
| 2007/0214759 A1 | 9/2007 | Merkel | |
| 2008/0146721 A1 | 6/2008 | Kaminsky et al. | |
| 2008/0153692 A1 | 6/2008 | Kimmich et al. | |
| 2008/0281122 A1 | 11/2008 | Augustine | |
| 2008/0287289 A1 | 11/2008 | Wang et al. | |
| 2008/0287703 A1 | 11/2008 | Wang et al. | |
| 2009/0093361 A1 | 4/2009 | Sakatani et al. | |
| 2010/0099552 A1 | 4/2010 | Fu et al. | |
| 2010/0121100 A1 | 5/2010 | Shay | |
| 2011/0144380 A1 | 6/2011 | Shay | |
| 2011/0190533 A1 | 8/2011 | Shay | |
| 2011/0306748 A1 | 12/2011 | Shay | |

FOREIGN PATENT DOCUMENTS

| | | |
|---|---|---|
| EP | 0455307 A1 | 11/1991 |
| EP | 0516262 A1 | 11/1991 |
| JP | 2001286733 A | 10/2001 |
| WO | WO2006094746 | 10/2001 |
| WO | 2006/127136 A1 | 11/2006 |
| WO | 2009/134398 A2 | 11/2009 |

OTHER PUBLICATIONS

Alvin B. Stiles, "Chapter 3. Supports Other Than Alumina," *Catalyst Supports and Supported Catalysts*, Butterworths Publishers, 1987, pp. 57-85.

David B. Braun and Meyer R. Rosen, *Rheology Modifiers Handbook: Practical Use and Application*, William Andrew Publishing, 2000, pp. 109-131.

C. E. Capes, "Particle Size Enlargement," Handbook of Powder Technology, vol. 1, Elsevier Scientific Publishing Company, 1980, pp. 112-122.

Aida Guitierrez-Alejandre, A Vibrational and Spectroscopic Study, WO3/TiO2-Al2O3 of Catalyst Precursors, Langmuir, vol. 14, No. 3, 1998, pp. 630-639.

* cited by examiner

*Primary Examiner* — Cam N. Nguyen

(57) ABSTRACT

An extrudate comprising titania, a carboxyalkyl cellulose, and a hydroxyalkyl cellulose is disclosed. The extrudates have a smooth outer surface when they exit the extruder. The extrusion processibility is improved.

13 Claims, No Drawings

TITANIA-CONTAINING EXTRUDATE

FIELD OF THE INVENTION

The invention relates to an extrudate comprising titania, a carboxyalkyl cellulose, and a hydroxyalkyl cellulose.

BACKGROUND OF THE INVENTION

Titania (or titanium dioxide) is a well-known white inorganic pigment. In addition to being a pigment, titania has other applications. For example, titania can be used as a catalyst or catalyst carrier (Stiles, A. B., "Supports Other Than Alumina," *Catalyst Supports and Supported Catalysts* (1987) Butterworths Publishers, pp. 57-85). Commercially, titania is produced as a fine powder. To be used as a catalyst or catalyst carrier, sometimes it is necessary to form titania into particles, such as spheres, tablets, extrudates, and the like. Despite many efforts in developing methods for producing titania extrudates, many of them are not suitable for commercial production because of their poor processibility. Therefore, there is a continued need to develop new processes for making titania extrudates, particularly as catalyst carrier (see, e.g., co-pending application [serial number has not yet been assigned] filed on Dec. 16, 2009).

SUMMARY OF THE INVENTION

The invention is an extrudate comprising titania, a carboxyalkyl cellulose, and a hydroxyalkyl cellulose; and a process for producing the extrudate comprising (a) mixing titania, a carboxyalkyl cellulose, and a hydroxyalkyl cellulose to form a dough; and (b) extruding the dough to produce the extrudate. The process has improved processibility and produces extrudates with a smooth outer surface.

DETAILED DESCRIPTION OF THE INVENTION

The invention is an extrudate comprising titania. Suitable titanias can be rutile, anatase, brookite, or a mixture. Titania may be produced by the chloride process, the sulfate process, the hydrothermal process, or the flame hydrolysis of titanium tetrachloride. Examples of suitable titanias include TiONA® DT-51, DT-52, DT-51D, DT-40, and DT-20 of Millennium Inorganic Chemicals.

The extrudate comprises a carboxyalkyl cellulose. Cellulose is an organic compound with the formula $(C_6H_{10}O_5)_n$, a polysaccharide consisting of a linear chain of $\beta$-1,4-linkages, as shown in Scheme I, where n=50 to 20,000. Cellulose is the structural component of the primary cell wall of green plants. Cellulose can be converted into many derivatives.

Scheme I

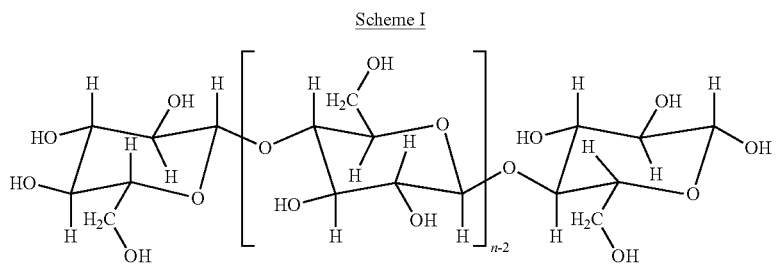

A carboxyalkyl cellulose is a cellulose derivative with carboxyalkyl groups bound to some of the hydroxyl groups of the glucopyranose monomers that make up the cellulose backbone, as shown in Scheme II, where R=H, carboxyalkyl, and m=50 to 20,000. It is often used as its sodium salt, sodium carboxyalkyl cellulose. The functional properties of carboxyalkyl celluloses depend on the degree of substitution of the cellulose structure (i.e., how many of the hydroxyl groups have taken part in the substitution reaction), as well as the chain length of the cellulose backbone and the degree of clustering of the substituents. The average number of substituted hydroxyl groups per glucose unit in cellulose derivatives is referred to as the degree of substitution (DS). Complete substitution would provide a DS of 3. Preferably, a carboxymethyl celluloses is used. Preferred carboxymethyl celluloses have a degree of substitution of 0.5 to 0.9 (D. B. Braun and M. R. Rosen, *Rheology Modifiers Handbook Practical Use and Applications* (2000) William Andrew Publishing, pp. 109-131). Carboxymethyl celluloses are known as extrusion aids (U.S. Pat. Nos. 5,884,138 and 6,709,570; U.S. Pat. Appl. Pub. No. 2008/0146721).

Scheme II

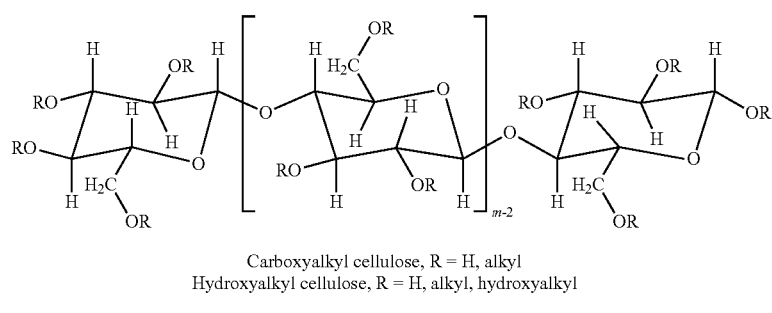

Carboxyalkyl cellulose, R = H, alkyl
Hydroxyalkyl cellulose, R = H, alkyl, hydroxyalkyl The extrudate also comprises a hydroxyalkyl cellulose. A hydroxyalkyl cellulose is a derivative of cellulose in which some of the hydroxyl groups in the repeating glucose units are hydroxyalkylated. Some of the hydroxyl groups in a hydroxyalkyl cellulose may also be alkylated. A typical structure of a hydroxyalkyl cellulose is shown in Scheme II, where R=H, alkyl, hydroxyalkyl, and m=50 to 20,000. Preferably, the hydroxyalkyl group is selected from the group consisting of 2-hydroxyethyl, 2-hydroxypropyl, and mixtures thereof. More preferably the hydroxyalkyl cellulose is alkylated. Most preferably, the hydroxyalkyl cellulose is selected from the group consisting of methyl 2-hydroxyethyl cellulose, methyl 2-hydroxypropyl cellulose, and mixtures thereof. Preferably, the degree of methyl substitution is from 1 to 2, more preferably from 1.5 to 1.8; and the 2-hydroxyethyl or 2-hydroxypropyl molar substitution is from 0.1 to 0.3. METHOCEL™ K4M cellulose derivative, a product of The Dow Chemical Company having a methyl substitution of 1.4 and a hydroxypropyl molar substitution of 0.21, is preferably used. Hydroxyalkyl celluloses are known as extrusion aids (U.S. Pat. Nos. 5,884,138, 6,316,383, and 6,709,570).

The extrudate may comprise an inorganic oxide other than titania, e.g., silicas, aluminas, zirconias, magnesias, silica-aluminas, silica-magnesias, zeolites, clays, and the like, and mixtures thereof. Suitable silicas include, e.g., silica gel, precipitated silica, and fumed silica. The weight ratio of other inorganic oxides to the titania is preferably less than 50:50, more preferably less than 20:80, most preferably less than 10:90.

The weight ratio of the carboxyalkyl cellulose to the titania is preferably from 0.2:100 to 5:100, more preferably from 0.5:100 to 4:100, most preferably from 1:100 to 3:100. The weight ratio of the hydroxyalkyl cellulose to the titania is preferably from 0.1:100 to 2.5:100, more preferably from 0.2:100 to 2:100, most preferably from 0.5:100 to 1:100. The weight ratio of the carboxyalkyl cellulose to the hydroxyalkyl cellulose is preferably from 5:1 to 1:2, more preferably from 3:1 to 1:1.

To produce the extrudate, the titania, the carboxyalkyl cellulose, and the hydroxyalkyl cellulose are made into a well-mixed dough. If necessary, a solvent may be used. Suitable solvents include water, alcohols, ethers, esters, amides, aromatic compounds, halogenated compounds, and the like, and mixtures thereof. Preferred solvents are water, alcohols, and their mixtures. Suitable alcohols include methanol, ethanol, isopropanol, tert-butanol, and benzyl alcohol.

A titania sol may be used as the source of the titania. A titania sol is a colloidal suspension of titania particles in a liquid. A titania sol can be prepared by hydrolyzing a titania precursor. Suitable titania precursors include titanium salts, titanium halides, titanium alkoxides, titanium oxyhalides, and the like.

The extrudate of the invention is made by extrusion, a process in which a dough is pushed through a die or an orifice to create long objects of a fixed cross-section. Extrusion is commonly used to process plastics or food, and to form adsorbents, catalysts, or catalyst carriers. Any conventional extruder may be used. A suitable screw-type extruder is described in "Particle Size Enlargement," *Handbook of Powder Technology*, vol. 1 (1980) pp. 112-22.

The carboxyalkyl cellulose and the hydroxyalkyl cellulose are used as extrusion aids. An extrusion aid helps the mixing, mulling, and extruding operation and may improve the mechanical and/or physical properties of the extrudate such as crushing strength, surface area, pore size, or pore volume. The extrudate comprising titania, the carboxyalkyl cellulose and the hydroxyalkyl cellulose has a smooth outer surface. They do not tend to stick to each other while being formed, dried, and calcined, which is suitable for large scale production. In addition the combination of the carboxyalkyl cellulose and the hydroxyalkyl cellulose minimizes "feathering." The term "feathering" means that an extrudate, instead of having a smooth outer surface, exhibits cracks in its surface where small flakes or "feathers" of the extrudate are separated from the surface. "Feathering" not only causes loss of valuable material but also tends to impair the physical strength of an extrudate.

The extrudate may comprise other extrusion aids, including, e.g., alkyl amines, carboxylic acids, alkyl ammonium compounds, amino alcohols, starch, polyacrylates, polymethacrylates, poly(vinyl alcohol)s, poly(vinylpyrrolidone)s, poly(amino acid)s, polyethers, poly(tetrahydrofuran)s, metal carboxylates, and the like, and mixtures thereof. Preferred poly(alkylene oxide)s are poly(ethylene oxide)s, poly(propylene oxide)s, or copolymers of ethylene oxide and propylene oxide. Organic extrusion aids are usually removed by calcination.

The extrudate is generally dried after it is formed. The drying operation generally removes most of the solvents (e.g., greater than 90%) from the extrudate. The drying operation may be performed at 30 to 200° C. at atmospheric pressure or under vacuum. The drying may occur in air or an inert atmosphere. Sometimes, it is preferable to raise the drying temperature slowly so the extrudate will not be cracked or weakened.

The invention includes a calcined extrudate. Preferably, the calcination is carried out in an oxygen-containing gas to burn off the organic materials (e.g., residual solvent and extrusion aids) contained in the extrudate. The calcination may be carried out at 400 to 1000° C., more preferably from 450 to 800°

C., most preferably from 650 to 750° C. Sometimes, it is beneficial to initially calcine the extrudate in an inert gas (e.g., nitrogen, helium) to thermally decompose the organic compounds contained in the extrudate, and then burn off the organic materials in an oxygen-containing gas. Generally, a calcined extrudate after the calcination contains less than 0.5 wt % carbon. Preferably, it contains less than 0.1 wt % carbon.

The invention additionally includes a process for producing an extrudate comprising (a) mixing titania, a carboxyalkyl cellulose, and a hydroxyalkyl cellulose to form a dough; (b) extruding the dough to produce the extrudate. The process is described in detail in the previous sections.

Example 1

D-T51 titania (2500 g), a high-purity WALOCEL™ C sodium carboxymethyl cellulose (The Dow Chemical Company, 52.5 g), poly(ethylene oxide) (MW=100,000, 35 g), and a 2-hydroxypropyl cellulose (METHOCEL™ K4M, 25 g) are mixed in an Eirich mixer for 5 min. Water (1005 g), an aqueous ammonium hydroxide (14.8 M, 100 g), and benzyl alcohol (17.5 g) are added into the mixer. They are mixed for 5 min at the "low" speed setting, then for 10 min at the "high" speed setting. The dough produced is placed in the hopper of a Bonnot 2-inch extruder (The Bonnot Company) equipped with a die face of 25 holes with a diameter of ⅛ inch. The extrusion is performed at a rate of approximately 0.25 kg/min. The extrudates produced have smooth outer surface and there is minimal sticking each other occurring. Almost no feathering is observed.

The extrudates are piled 1 inch deep on a collection tray and dried in air at 80° C. for 12 h, then calcined in air. The calcination temperature is raised from room temperature to 500° C. at a rate of 2° C./min, held at 500° C. for 2 h, raised from 500° C. to 700° C. at a rate of 10° C./min, held at 700° C. for 3 h, then lowered to room temperature.

Some physical properties of the calcined titania extrudate are listed in Table 1. The crush strength of the calcined titania extrudate is measured with a Chatillon crush strength analyzer (Model DPP 50). The force necessary for failure in 25 measurements is averaged to give the reported value. Bulk density is measured by placing 40 g of the calcined extrudates in a 100-mL graduated cylinder (1" nominal outer diameter). The graduated cylinder is tapped until the apparent volume no longer changes, and then this value is divided into the mass to calculate the bulk density. Voidage is determined by adding the pellets to 50 mL water in a second graduated cylinder and then tapping until all voids are filled. The resulting water level is subtracted from the total volume of the water and the pellets taken separately to determine the void volume occupied by water. Total pore volume is determined by pouring the mixture through a sieve basket, shaking to remove excess water and then weighing the wet extrudates. The increase in mass over the initial 40 g of extrudates divided by the density of water is taken as the measure of the pore volume.

Comparative Example 2

The procedure of Example 1 is repeated with the formulation shown in Table 1. The extrudates are droopy as they exit the die face of the extruder and tend to stick to each other as they lay on the collection tray.

Comparative Example 3

The procedure of Example 1 is repeated with the formulation shown in Table 1. The extrudates are droopy as they exit the die face of the extruder and tend to stick to each other as they lay on the collection tray.

TABLE 1

|  | Example | | |
| --- | --- | --- | --- |
|  | 1 | C. 2 | C. 3 |
| Formulation |  |  |  |
| Titania (g) | 2500 | 2500 | 2500 |
| Water (g) | 1005 | 1250 | 1005 |
| Poly(ethylene oxide) (g) | 35 | 35 | 35 |
| WALOCEL ™ C cellulose (g) | 52.5 | 52.5 | 52.5 |
| Benzyl alcohol (g) | 17.5 | 17.5 | 17.5 |
| Ammonium hydroxide (g) | 100 | 100 | 100 |
| METHOCEL ™ K4M cellulose (g) | 25 | 0 | 0 |
| Extrusion Processibility | good | poor | poor |
| Properties of Calcined Extrudate |  |  |  |
| Crushing strength (lb/mm) | 1.68 | 1.37 | 1.43 |
| Surface area (m²/g) | 27.2 | n/a | n/a |
| Pore volume (mL/g) | 0.32 | 0.30 | 0.30 |

Comparative Example 4

The procedure of Example 1 is repeated, except that the formulation is as follows: DT-51 (2000 g), TAMOL™ 1124 dispersant (a hydrophilic polyelectrolyte copolymer from The Dow Chemical Company, 32.6 g), METHOCEL™ K4M (54.6 g), lactic acid (6 g), water (950 g), aqueous ammonium hydroxide (14.8 M, 70 g).

Comparative Example 5

The procedure of Example 4 is repeated, except that alumina (DISPERAL® P2, available from Sasol, 20 g) is used. The extrudates are droopy as they exit the die face of the extruder and tend to stick to each other as they lay on a metal tray. The calcined extrudate contains 1 wt % alumina and 99 wt % titania.

TABLE 2

|  | Example | |
| --- | --- | --- |
| Formulation | C. 4 | C. 5 |
| DT-51 titania (g) | 2000 | 2000 |
| METHOCEL ™ K4M cellulose (g) | 54.6 | 54.6 |
| TAMOL ™ 1124 dispersant (g) | 32.6 | 32.6 |
| Water (g) | 950 | 950 |
| Ammonium hydroxide solution (g) | 70 | 70 |
| DISPERAL ® P2 alumina (g) | 0 | 20 |
| Lactic acid (g) | 60 | 60 |
| Extrusion Processibility | poor | poor |

Example 6

The procedure of Example 1 is repeated, except that the formulation is as follows: DT51 (300 g), TAMOL™ 1124 dispersant (5 g), WALOCEL™ C cellulose (6 g), METHOCEL™ K4M cellulose (6 g), lactic acid (4.5 g), water (155 g), and aqueous ammonium hydroxide (14.8 M, 11 g). The extrudates have smooth outer surface. Minimal feathering is observed. Almost no extrudate is observed to stick to others.

Comparative Example 7

The procedure of Example 6 is repeated, except that the formulation is shown in Table 3. The extrudates slump upon exiting the die. They stick to each other on the collection tray.

Comparative Example 8

The procedure of Example 6 is repeated, except that the formulation is shown in Table 3. The extrudates do not tend to stick to each other after laying the on the collection tray. However, they appear to be feathering.

TABLE 3

| Formulation | Example | | |
|---|---|---|---|
| | 6 | C. 7 | C. 8 |
| DT-51 titania (g) | 300 | 300 | 300 |
| Water (g) | 155 | 145 | 145 |
| TAMOL ™ 1124 dispersant (g) | 5 | 5 | 5 |
| WALOCEL ™ C cellulose (g) | 6 | 0 | 6 |
| Lactic acid (g) | 4.5 | 4.5 | 4.5 |
| Ammonium hydroxide (g) | 11 | 11 | 11 |
| METHOCEL ™ K4M cellulose (g) | 6 | 6 | 0 |
| Extrusion Processibility | good | poor | poor |

Example 9

$NaHCO_3$ powder (27 g) is slowly added to an aqueous solution containing $Na_2PdCl_4 \cdot 3H_2O$ (31.4 g), $NaAuCl_4 \cdot 2H_2O$ (11.3 g), and water (235.4 g). The mixture is stirred at room temperature for 10 min. The solution is sprayed with a pipette on calcined titania extrudates prepared in Example 1 (1000 g) while they are being tumbled in a rotating flask. Once the impregnation is finished, the rotating flask is heated to about 100° C. with a heat gun. The impregnated extrudates are tumbled for another 30 min at 100° C., then placed in an oven at 80° C. for 2 h before they are cooled to room temperature.

The dried extrudates are washed with warm water (50-80° C.) until no chloride can be detected by mixing the wash filtrate solution with a 1 wt % silver nitrate solution to observe precipitation. After washing is finished, the catalyst is dried at 80 to 100° C. to remove water. Then they are heated at 230° C. for 3 h in air, and at 230° C. for 30 min under a nitrogen flow. The temperature is raised to 500° C. under a flow of 10 mol % hydrogen in nitrogen gas, and held for 3 h before it is cooled to room temperature.

The extrudates are washed with an aqueous solution containing 10 wt % potassium acetate and 1 wt % potassium hydroxide (10 L). The washed extrudates are dried under nitrogen at 125° C. for 2 h. A palladium-gold catalyst is obtained. It contains 0.93 wt % Pd, 0.54 wt % Au, and 1.5 wt % K.

Example 10

The palladium-gold catalyst prepared in Example 9 is tested for vinyl acetate production in a fixed-bed reactor (stainless steel, 1 inch O.D.). The reactor is charged with a mixture of the catalyst (10 g) and an inert alpha alumina cylindrical pellets (⅛" in diameter, surface area 4 m²/g, pore volume 0.25 mL/g, 25 g). The feed contains 46.1 mol % helium, 33.9 mol % ethylene, 11.48 mol % acetic acid, 4.2 mol % oxygen, and 4.2 mol % nitrogen. The reactor pressure is 80 psig and the space velocity relative to the volume of the catalyst is 3050 $h^{-1}$ at standard temperature and pressure. The reactor is cooled using a fluidized sand bath, the temperature of which is set at 130° C. The product stream is analyzed by gas chromatography (GC). Oxygen conversion, oxygen selectivity, oxygen yield to vinyl acetate, and ethylene selectivity to vinyl acetate between 75 to 100 h on stream are calculated from the GC results and listed in Table 4. Oxygen conversion is calculated by dividing the amount of oxygen consumed by the total amount of oxygen fed to the reactor. Oxygen selectivity to vinyl acetate is the amount of oxygen consumed in making vinyl acetate divided by the total amount of oxygen consumed. Oxygen yield to vinyl acetate is the product of oxygen conversion multiplied by oxygen selectivity. Ethylene selectivity to vinyl acetate is the amount of ethylene consumed in making vinyl acetate divided by the total amount of ethylene consumed. Catalyst productivity is the grams of vinyl acetate produced per liter of the catalyst per hour.

TABLE 4

| Oxygen conversion (%) | 63.7 |
|---|---|
| Oxygen selectivity to vinyl acetate (%) | 86.3 |
| Oxygen yield to vinyl acetate (%) | 54.9 |
| Ethylene selectivity to vinyl acetate (%) | 97.4 |
| Catalyst productivity (g · $L^{-1}$ · $h^{-1}$) | 492.2 |

I claim:

1. An extrudate comprising titania, a carboxyalkyl cellulose, and a hydroxyalkyl cellulose, wherein the weight ratio of carboxyalkyl cellulose to titania is from 1:100 to 3:100 and the weight ratio of hydroxyalkyl cellulose to titania is from 0.5:100 to 1:100.

2. The extrudate of claim 1 wherein the carboxyalkyl cellulose is a carboxymethyl cellulose.

3. The extrudate of claim 1 having a carboxyalkyl cellulose to hydroxyalkyl cellulose weight ratio of from 5:1 to 1:2.

4. The extrudate of claim 1 having a carboxyalkyl cellulose to hydroxyalkyl cellulose weight ratio of from 3:1 to 1:1.

5. The extrudate of claim 1 wherein the hydroxyalkyl cellulose is selected from the group consisting of 2-hydroxypropyl cellulose, 2-hydroxethyl cellulose, and mixtures thereof.

6. The extrudate of claim 1 wherein the hydroxyalkyl cellulose is selected from the group consisting of methyl 2-hydroxypropyl cellulose, methyl 2-hydroxethyl cellulose, and mixtures thereof.

7. The extrudate of claim 1 wherein the titania constitutes at least 10 weight percent of the extrudate.

8. The extrudate of claim 1 further comprising an inorganic oxide other than titania.

9. The extrudate of claim 8 having an inorganic oxide to titania weight ratio of less than 10:90.

10. The extrudate of claim 1 having a smoother outer surface than an extrudate not comprising the carboxyalkyl cellulose and the hydroxyalkyl cellulose.

11. The extrudate of claim 1 having less feathering than an extrudate not comprising the carboxyalkyl cellulose and the hydroxyalkyl cellulose.

12. The extrudate of claim 1 wherein the extrudate sticks to each other less than an extrudate not comprising the carboxyalkyl cellulose and the hydroxyalkyl cellulose.

13. The extrudate of claim 1 is more suitable for large scale production than an extrudate not comprising the carboxyalkyl cellulose and the hydroxyalkyl cellulose.

* * * * *